US011096528B2

(12) United States Patent
Chacon, Jr.

(10) Patent No.: US 11,096,528 B2
(45) Date of Patent: Aug. 24, 2021

(54) HYGIENE MAINTENANCE WRISTBAND

(71) Applicant: Bernardo Garu Chacon, Jr., Hollywood, FL (US)

(72) Inventor: Bernardo Garu Chacon, Jr., Hollywood, FL (US)

(*) Notice: Subject to any disclaimer, the term of this patent is extended or adjusted under 35 U.S.C. 154(b) by 0 days.

(21) Appl. No.: 16/781,862

(22) Filed: Feb. 4, 2020

(65) Prior Publication Data

US 2020/0245822 A1    Aug. 6, 2020

Related U.S. Application Data

(60) Provisional application No. 62/800,986, filed on Feb. 4, 2019.

(51) Int. Cl.
| | |
|---|---|
| *A47K 5/12* | (2006.01) |
| *G06F 1/16* | (2006.01) |
| *A44C 5/00* | (2006.01) |

(52) U.S. Cl.
CPC .......... *A47K 5/1201* (2013.01); *A44C 5/0007* (2013.01); *A47K 5/1217* (2013.01); *G06F 1/163* (2013.01)

(58) Field of Classification Search
CPC .. A47K 5/1201; A47K 5/0007; A47K 5/1217; G06F 1/163
USPC ........................................................ 222/175
See application file for complete search history.

(56) References Cited

U.S. PATENT DOCUMENTS

| | | | |
|---|---|---|---|
| 2,235,350 A | 3/1941 | Anderson | |
| 6,415,960 B1 | 7/2002 | Fink et al. | |
| 7,135,011 B2 | 11/2006 | Powers et al. | |
| 7,316,332 B2 | 1/2008 | Powers et al. | |
| 9,578,935 B2* | 2/2017 | Horgan | ................ A47K 5/1201 |
| 2006/0289567 A1* | 12/2006 | Shoham | ................. A61B 90/80 |
| | | | 222/175 |
| 2008/0067193 A1* | 3/2008 | Powers | .................. A45D 34/00 |
| | | | 222/175 |
| 2009/0008411 A1* | 1/2009 | Schumacher | ....... A01M 1/2055 |
| | | | 222/175 |
| 2011/0155765 A1* | 6/2011 | Properzi | .............. A47K 5/1201 |
| | | | 222/175 |

(Continued)

FOREIGN PATENT DOCUMENTS

| | | |
|---|---|---|
| BE | 896577 A | 8/1983 |
| EP | 0576629 A4 | 2/1994 |

*Primary Examiner* — Vishal Pancholi

(57) ABSTRACT

A hygiene maintenance wristband is an apparatus that allows a user to easily maintain the hygiene while on-the-go. The apparatus includes a band, a first casing, a second casing, a solution dispenser, and a clasp mechanism. The band attaches the first casing and the second casing around the wrist of a user. The first casing houses the solution dispenser. The clasp mechanism is integrated within the second casing in order to connect and disconnect the band. The clasp mechanism also adjusts the overall length of the band around a wrist. The apparatus further includes a dispenser-release mechanism so that the solution dispenser may be released from the first casing. The apparatus preferably includes a portable computing device as well in order to further monitor the wellbeing of the user. The apparatus further includes a floss-dispensing mechanism in order to maintain oral hygiene.

17 Claims, 6 Drawing Sheets

(56) References Cited

U.S. PATENT DOCUMENTS

| | | | |
|---|---|---|---|
| 2012/0138637 A1* | 6/2012 | Ciavarella | A61L 2/18 222/175 |
| 2012/0282011 A1* | 11/2012 | Francois | A61L 2/18 401/196 |
| 2014/0230960 A1 | 8/2014 | Ciavarella et al. | |
| 2017/0156454 A1* | 6/2017 | Abadi | A47K 5/1204 |
| 2018/0192832 A1* | 7/2018 | Shaukat | A44C 5/14 |

* cited by examiner

HYGIENE MAINTENANCE WRISTBAND

The current application claims a priority to the U.S. provisional patent application Ser. No. 62/800,986 filed on Feb. 4, 2019.

FIELD OF THE INVENTION

The present invention generally relates to hygiene tools. More specifically, the present invention is a hygiene maintenance wristband.

BACKGROUND OF THE INVENTION

In present times, individuals are known to use a plethora of unique chemical compounds in their lives. Lotions, ointments, atomized perfumes, repellants, sanitizers, etc. are all commonly deployed from their respective containers on a daily basis. Even dental care has been made portable, with small brushed and travel-sized toothpaste tubes being commonly found in bags of travelers, pockets, and purses. With the endless number of compounds that an individual may wish to carry and use on a daily basis, it quickly becomes apparent that they may not all be carried on one's person. The sheer volume of retail-sized containers carrying such a variety of products would quickly fill an entire backpack, if not more. It may similarly be impractical to simply buy "travel-size" containers of such products, given the added expense and absolute unavailability of such packaging for many aerosol products. Additionally, the need to cycle through such a wide variety of possible applicable substance is time consuming and unwieldly, discouraging their use altogether.

The present invention aims to allow a user to carry and deploy an unlimited variety of semi-solid, liquid, gelatinous, or atomized products by re-sealing said products inside a dedicated storage and deployment solution. The present invention will enable users to quickly and directly deploy said compounds to target areas via a wearable watch-type device that can carry and deploy multiple different compounds interchangeably. A means of reloading the expended components of the present invention via a universal tool suitable for attachment to any known retail-size container, in addition to a carrying case, dedicated refill tool, and a variety of possible storage solutions are contemplated. The present invention will additionally feature aspect typically associated with "smart" devices such as telecommunications, text messaging, media playback, and other features understood in the industry.

DETAIL DESCRIPTIONS OF THE INVENTION

Figure 1:
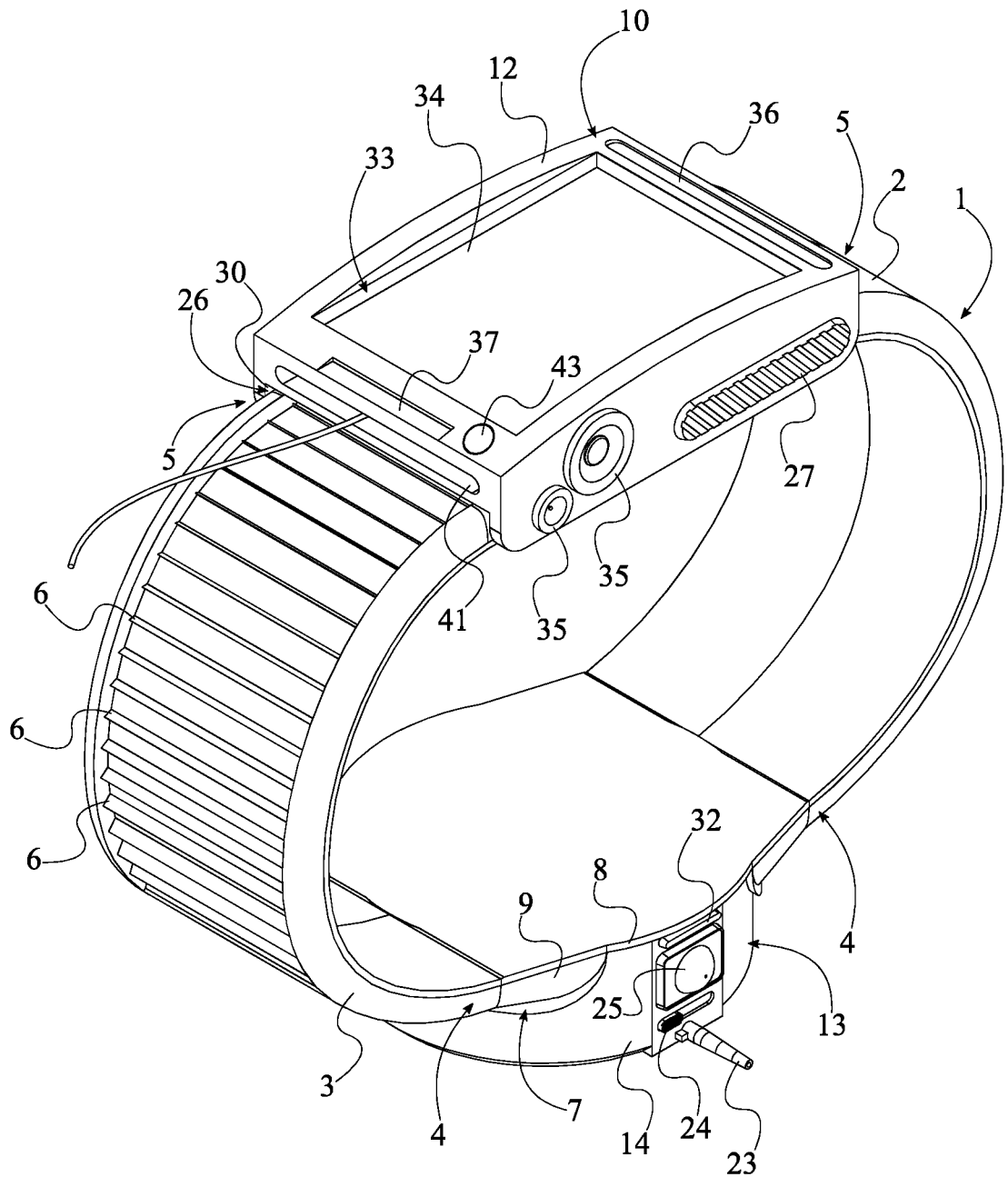
FIG. 1 is a top perspective view of the preferred embodiment of the present invention with a portable computing device integrated with a second casing.

All illustrations of the drawings are for the purpose of describing selected versions of the present invention and are not intended to limit the scope of the present invention.

The present invention is a hygiene maintenance wristband 1 that deploys a variety of hygiene solutions that maintain personal hygiene. The present invention is refillable, and the solutions are interchangeable. The present invention is preferably worn around the wrist for quick and easy accessibility. In order for the present invention to be worn around the wrist while comfortably supply a variety of hygiene solutions the present invention comprises a band 1, a first casing 7, a second casing 10, a solution dispenser 13, and a clasp mechanism 26, seen in FIG. 1 and FIG. 2. The band 1 wraps the first casing 7 and the second casing 10 around the wrist of the user. Furthermore, the band 1 comprises a fixed member 2 and an adjustable member 3. The fixed member 2 keeps the first casing 7 and the second casing 10 connected with each other. The adjustable member 3 changes the length of the overall band 1 with the clasp mechanism 26 in order to accommodate various sized wrists. The first casing 7 retains the solution dispenser 13, and the second casing 10 houses the clasp mechanism 26. The first casing 7 and the second casing 10 are both preferably waterproof. The solution dispenser 13 houses hygiene solution which may include, but is not limited to, topical skin creams, hand sanitizer, perfume, cologne, and lotions. The clasp mechanism 26 attaches the adjustable member 3 with the second casing 10 and accommodates the lengthening and shortening of the adjustable member 3.

The overall arrangement of the aforementioned components allows the present invention to deploy a variety of hygiene solutions while being worn around the wrist. A first end 4 of the adjustable member 3 and a first end 4 of the fixed member 2 are fixed with the first casing 7, thereby integrating the first casing 7 into the band 1. The band 1 is continuous around the wrist of the user as the first end 4 of the adjustable member 3 is positioned opposite the first end 4 of the fixed member 2 about the first casing 7. A second end 5 of the fixed member 2 is connected with the second casing 10, thereby integrating the second casing 10 into the band 1. The wrist of the user may be placed within the band 1 as the second end 5 of the adjustable member 3 is operatively coupled with the second casing 10 by the clasp mechanism 26, wherein the clasp mechanism 26 is used to readily connect or readily disconnect the adjustable member 3 to the second casing 10. Moreover, the clasp mechanism 26 is used to lengthen or shorten a combined circumference of the band 1, thereby serving as a universal hygiene tool for a variety of users.

Figure 2:
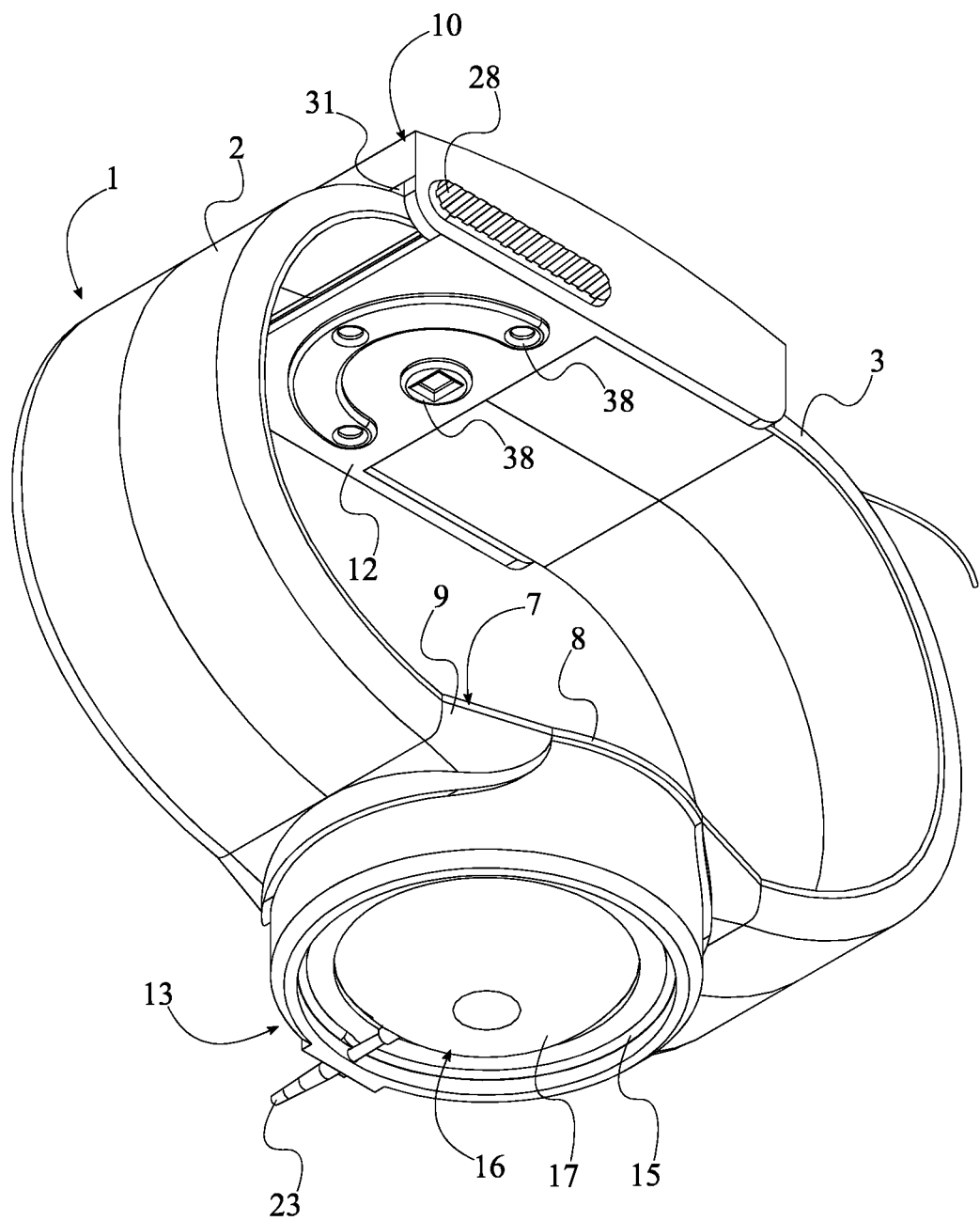
FIG. 2 is a bottom perspective view of the preferred embodiment of the present invention with the portable computing device integrated with the second casing.
Figure 5:
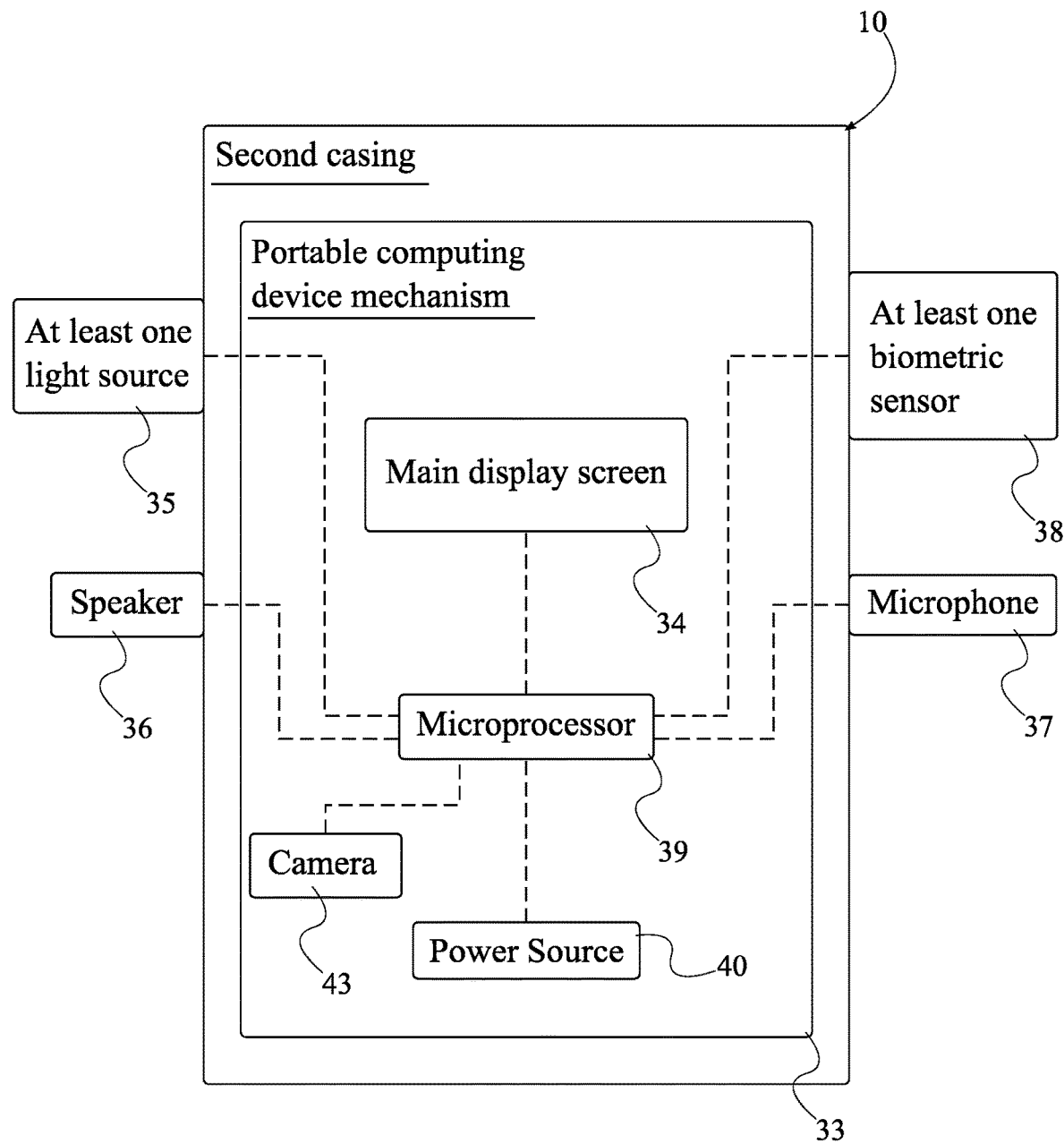
FIG. 5 is a schematic view of the electronic connections of the present invention.

In order for the clasp mechanism 26 to provide a secure connection between the adjustable member 3 and the second casing 10 while being able to vary the combined circumference of the band 1, the clasp mechanism 26 comprises a main release button 27, a safety release button 28, a ratchet mechanism 29, a first slot 30, and a second slot 31, seen in FIG. 1, FIG. 2, and FIG. 5. The main release button 27 and the safety release button 28 allows only the purposeful separation of the adjustable member 3 with the second casing 10. The ratchet mechanism 29 allows for the combined circumference to be adjusted. The adjustable member 3 is engaged with the ratchet mechanism 29 through the first slot 30, and the fixed member 2 is secured within the second casing 10 through the second slot 31. In order for the adjustable member 3 to be secured with the ratcheting mechanism, the band 1 comprises a plurality of tracks 6. The plurality of tracks 6 secures the adjustable member 3 with the second casing 10 for any size of the combined circumference of the band 1. The adjustable member 3 defines the combined circumference of the band 1 as the plurality of tracks 6 is integrated along the adjustable member 3. The main release button 27 and the safety release button 28 are positioned opposite each other about the second casing 10 in order to require the second casing 10 to be pressed along both sides to release the ratchet mechanism 29. The main release button 27 and the safety release button 28 are easily accessible by a user as the main release button 27 and the safety release button 28 are externally integrated into the second casing 10. The first slot 30 laterally traverses into the second casing 10, and the second slot 31 laterally traverses into the second casing 10, opposite the first slot 30 so that the band 1 is continuous around the wrist of the user. The second end 5 of the fixed member 2 is connected within the second slot 31. A wrist is easily positioned and secured within the band 1 as the second end 5 of the adjustable member 3 is operatively coupled within the first slot 30 by an engagement between the ratchet mechanism 29 and the plurality of tracks 6, wherein the ratchet mechanism 29 is used to readily engage or readily disengage the plurality of tracks 6. The main release button 27 and the safety release button 28 are operatively coupled with the ratchet mechanism 29, wherein the main release button 27 and the safety button are simultaneously pressed in order to release the ratchet mechanism 29. This engagement serves as a safety lock between the adjustable member 3 and the second casing 10.

In order for the solution dispenser 13 to be securely housed within the first casing 7 and be readily separated from the first casing 7, the present invention comprises a dispenser-release mechanism 32. In the preferred embodiment of the present invention, the dispenser-release mechanism 32 is a snap lock. The first casing 7 also comprises a base wall 8 and a lateral wall 9, seen in FIG. 1 and FIG. 2. The base wall 8 connects the adjustable member 3 and the fixed member 2 with the first casing 7. The lateral wall 9 surrounds the solution dispenser 13 and houses the dispenser-release mechanism 32. The solution dispenser 13 further comprises a frame 14, an annular retainer 15, and at least one pod 16, seen in FIG. 1, FIG. 2, and FIG. 3. The frame 14 houses the annular retainer 15 and the at least one pod 16 within the solution dispenser 13. The annular retainer 15 secures the at least one pod 16 within the frame 14. The at least one pod 16 contains a hygiene solution. The base wall 8 is positioned adjacent with the lateral wall 9, and the lateral wall 9 is perimetrically fixed around the base wall 8 in order to effectively house the solution dispenser 13 when connected with the first casing 7. The frame 14 is positioned within the lateral wall 9, and the annular retainer 15 is mounted onto the frame 14 and is removably attached around the at least one pod 16. This arrangement allows the entire solution dispenser 13 to be separated from the first casing 7. The solution dispenser 13 is securely attached within the first casing 7 and is easily separated as the frame 14 is operatively coupled with the lateral wall 9 by the dispenser-release mechanism 32, wherein the dispenser-release mechanism 32 is used to lock or unlock the frame 14 with the lateral wall 9. The solution dispenser 13 may be engaged while disconnected from the first casing 7.

Figure 3:
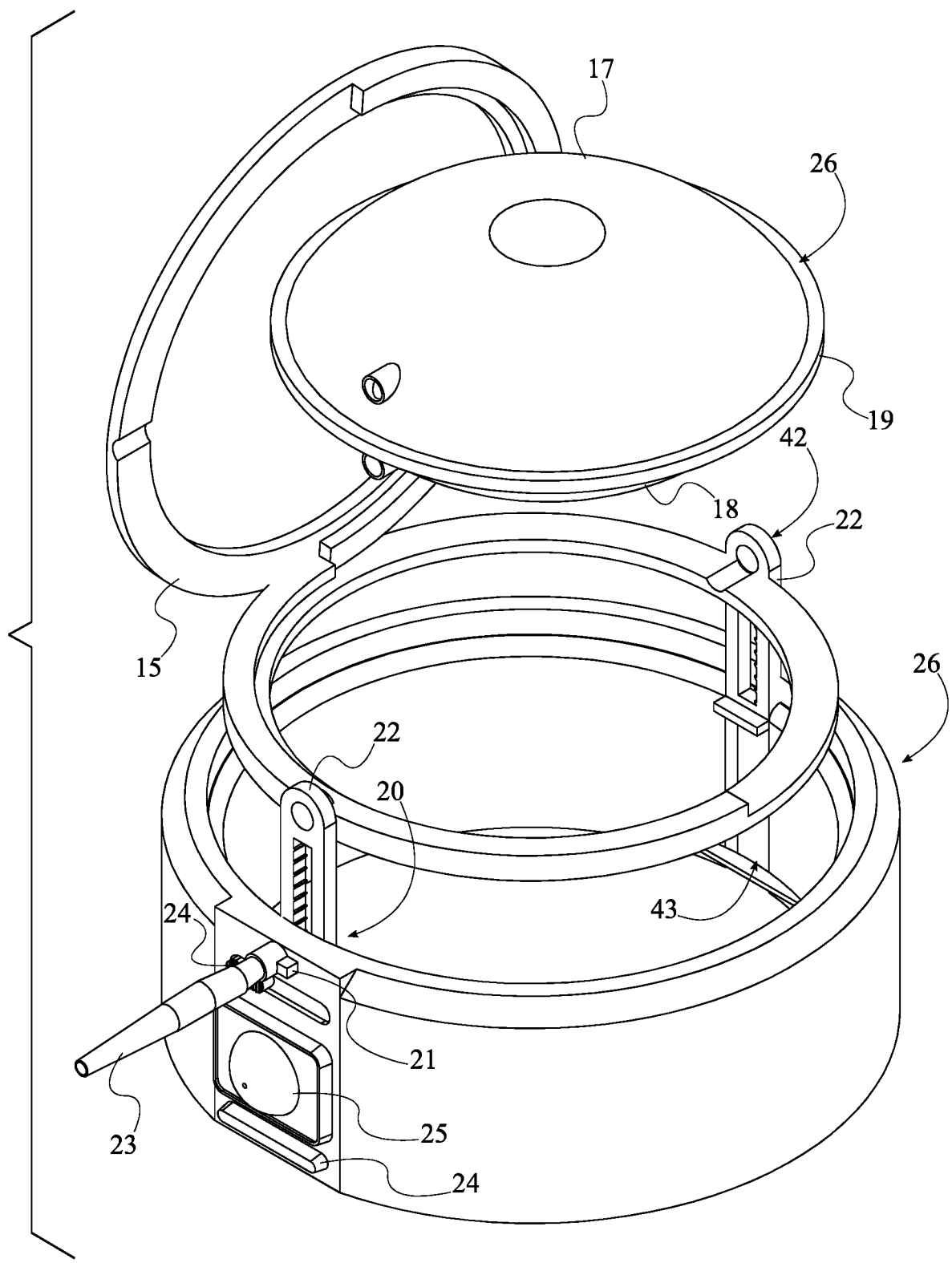
FIG. 3 is an exploded view of a solution dispenser of the present invention.
Figure 4:
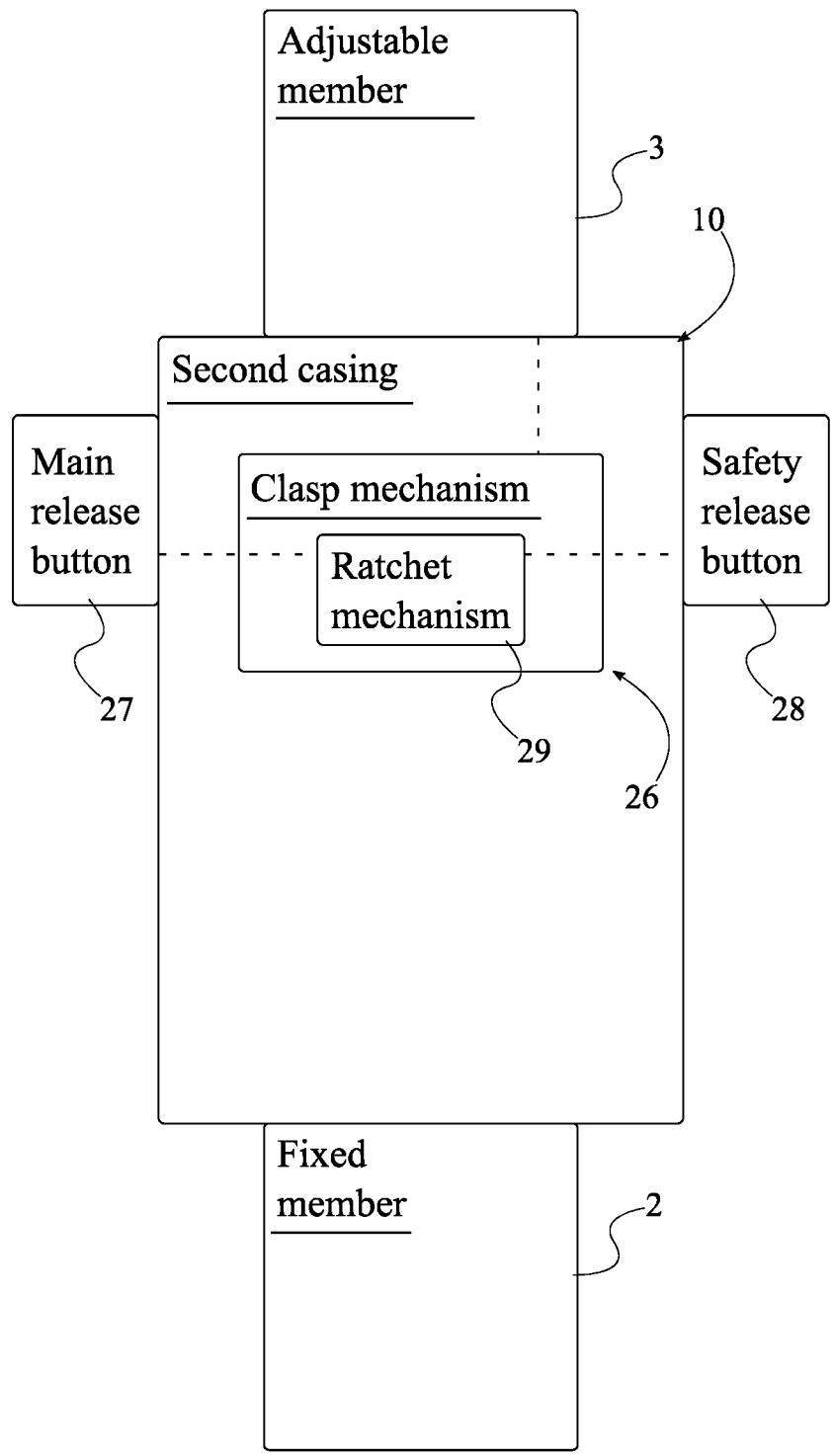
FIG. 4 is a schematic view of a clasp mechanism of the present invention.

The solution dispenser 13 further comprises a pod-releasing mechanism 20, a retractable nozzle 23, and a release switch 24 in order remove or access the at least one pod 16 positioned within the frame 14, also seen in FIG. 1, FIG. 2, and FIG. 3. The pod-releasing mechanism 20 retracts and ejects the at least one pod 16. In the preferred embodiment of the present invention, the pod-releasing mechanism 20 is automatic. The retractable nozzle 23 dispenses the hygiene solution contained within the retractable nozzle 23. Moreover, the retractable nozzle 23 serves as a latch or lock for the pod-releasing mechanism 20. The release switch 24 allows a user to manually operate the pod-releasing mechanism 20. In order for the at least one pod 16 to be secured with the frame 14, the annular retainer 15 is attached around the at least one pod 16. The annular retainer 15 is operatively coupled to the frame 14 by the pod-releasing mechanism 20, wherein the pod-releasing mechanism 20 is used to extend the frame 14 out of the second casing 10 and is used to then rotate the annular retainer 15, thereby facilitating the access of the at least one pod 16. The release switch 24 is operatively coupled to the pod-releasing mechanism 20, wherein the release switch 24 is used to actuate the pod-releasing mechanism 20 so that the user simply engages the release switch 24 to access the at least one pod 16. In the preferred embodiment of the present invention, the at least one pod 16 with the annular retainer 15 is retracted into frame 14 with a simple push of the annular retainer 15 to again active the pod-releasing mechanism 20. It is understood that various embodiments of the present invention may further comprises a switch that automatically retracts the at least one pod 16 with the annular retainer 15 back into the frame 14. In order to maintain the compact and ergonomic structure of the present invention, the retractable nozzle 23 is telescopic. This arrangement protects the retractable nozzle 23 from accidently getting snagged and breaking while not being used to dispense hygiene solution.

In order to automatically access the at least one pod 16, the pod-releasing mechanism 20 comprises a control button 21 and a couple of rail assemblies 22, seen in FIG. 3. The control button 21 activates the couple of rail assemblies 22, and the couple of rail assemblies 22 slide the annular retainer 15 into and out of the frame 14. Each of the couple of rail assemblies 22 comprises a stopper end 42 and a rotation end 43. The stopper end 42 prevents the annular retainer 15 from retracting through the frame 14, and the rotation end 43 is the rotation axis for the annular retainer 15. The stopper end 42 is positioned opposite the rotation end 43 along the rail assembly in order for the annular retainer 15 to freely and continuously rotate. More specifically, the annular retainer 15 is rotatably mounted with the rotation end 43. The control button 21 is externally mounted with the frame 14, allowing a user to engage with the control button 21. The at least one pod 16 exits and enters the frame 14 with the annular retainer 15 as the at least one pod 16 is slidably engaged along the couple of rail assemblies 22. The pod-releasing mechanism 20 is automatic as control button 21 is operatively coupled to the rotation end 43 of each of the couple of rail assemblies 22, wherein the control button 21 is used to actuate the rotation end 43 and is consequently used to flip the at least one pod 16.

Before the application of any hygiene solution within the at least one pod 16, the surface or area may be checked for any germs or bacteria as the solution dispenser 13 further comprises a bacteria-detecting light source 25, seen in FIG. 1 and FIG. 3. The bacteria-detecting light source 25 is preferably a blacklight, however, alternate embodiments of the bacteria-light source may be an ultraviolet light. The bacteria-detecting light source 25 is externally integrated with the frame 14 effectively illuminating a desired area positioned adjacent the retractable nozzle 23.

The at least one pod 16 may dispense more than one hygiene solution as the at least one pod 16 comprises a first retaining portion 17, a second retaining portion 18, and a disk plate 19, seen in FIG. 3. The first retaining portion 17 and the second retaining portion 18 each contain hygiene solutions that are preferably different from one another. The disk plate 19 connects the first retaining portion 17 with the second retaining portion 18. The first retaining portion 17 is mounted onto the disk plate 19. The second retaining portion 18 is mounted onto the disk plate 19, opposite the first retaining portion 17. This arrangement allows the retractable nozzle 23 to engage with both the first retaining portion 17 and the second retaining portion 18 upon the engagement of the pod-releasing mechanism 20.

In alternate embodiments of the present invention, a spray nozzle may be mounted adjacent the retractable nozzle 23, opposite the at least one pod 16. The spray nozzle evenly distributed a hygiene solution as a spray. The hygiene solution is preferably perfume or cologne. In further embodiments of the present invention, the at least one pod 16 is refillable. The at least one pod 16 is preferably refilled with a solution pen that comprises a reservoir of hygiene solution. The solution pen refills the at least one pod 16 through an outlet with the retractable nozzle 23. In further embodiments of the present invention, the at least one pod 16 with a first retaining portion 17 and a second retaining portion 18 further comprises a first identifying marker and a second identifying marker. The first identifying marker labels the first retaining portion 17 with the hygiene solution within the first retaining portion 17. Similarly, the second identifying marker labels the second retaining portion 18 with hygiene solution within the second retaining portion 18.

Figure 6:
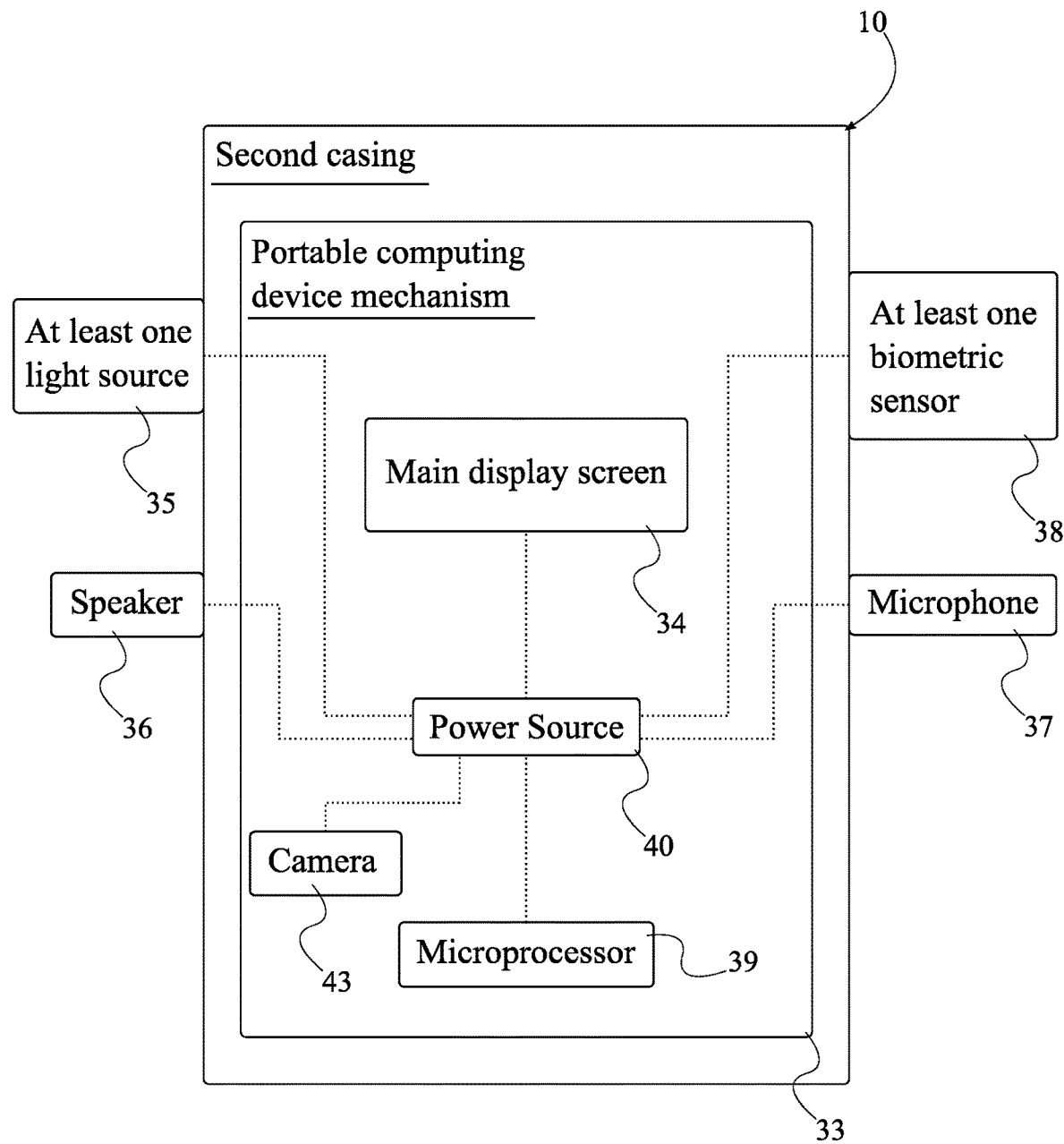
FIG. 6 is a schematic view of the electrical connections of the present invention.

The present invention further monitors and enhances the overall wellbeing of user as the present invention preferably comprises a portable computing device 33, seen in FIG. 1, FIG. 5, and FIG. 6. The portable computing device 33 is preferably a smart watch. The smart watch may be permanently connected within the band 1 or interchangeable. The portable computing device 33 comprises a main display screen 34, at least one light source 35, a speaker 36, a microphone 37, a camera 43, at least one biometric sensor 38, a microprocessor 39, and a power source 40. The main display screen 34 allows a user to engage with the at least one light source 35, the speaker 36, the microphone 37, the camera 43, and the at least one biometric sensor 38. The at least one light source 35 illuminates an area for the application of a hygiene solution. The at least one light source 35 may also identify germs and bacteria of a desired surface for application. The speaker 36 emits audio and the microphone 37 allows the user to communicate verbally or transmit and record an audio file. The camera 43 allows for video calls and video messages. The speaker 36 and microphone 37 provide a phone call feature for the portable computing device 33. The at least one biometric sensor 38 monitors the vitals of a user that aid in the overall wellbeing of the user. The at least one biometric sensor 38 may be a heart rate monitor and a calorie counter. The microprocessor 39 manages the electronic functions of the portable computing device 33, and the power source 40 provides the necessary power for the portable computing device 33. The power source 40 may be recharged with an external power supply.

The overall arrangement of the components for the portable computing device 33, seen in FIG. 1, FIG. 2, FIG. 5, and FIG. 6, allows the portable computing device 33 to both monitor vitals of the user and function as a smart watch. In order to engage the main display screen 34, the speaker 36, the microphone 37, and the camera 43, the main display screen 34, the speaker 36, the microphone 37, and the camera 43 are externally integrated into a first flat surface 11 of the second casing 10. The first flat surface 11 of the second casing 10 is oriented away from the wrist of the user so that the main display screen 34, the speaker 36, the microphone 37, and the camera 43 are readily accessible. A second flat surface 12 is positioned opposite the first flat surface 11 about the second casing 10, seen in FIG. 2. The second flat surface 12 presses against the wrist of the user. The at least one biometric sensor 38 is externally integrated into the second flat surface 12 in order for the at least one biometric sensor 38 to be readily able to detect the vitals of the user. The at least one light source 35 is laterally mounted with the second casing 10 in between the first flat surface 11 and the second flat surface 12 in order for the user to easily maneuver the direction of the at least one light source 35 while being worn around the wrist. The microprocessor 39 and the power source 40 are mounted within the second casing 10 to contain and protect the microprocessor 39 and the power source 40. In order to operate the portable computing device 33, the microprocessor 39 is electronically connected with the main display screen 34, the at least one light source 35, the speaker 36, the microphone 37, the camera 43, the at least one biometric sensor 38, and the power source 40. The portable computing device 33 is able to perform a variety of functions as the power source 40 is electrically connected with the main display screen 34, the at least one light source 35, the speaker 36, the microphone 37, the camera 43, the at least one biometric sensor 38, and the microprocessor 39.

The preferred embodiment of the present invention further comprises a floss-dispensing mechanism 41 in order to better maintain oral hygiene. The floss-dispensing mechanism 41 is laterally integrated into the second casing 10 so floss is easily taken from the second casing 10 while the main display screen 34 remains visible and may encompass a larger area across the second casing 10.

Although the invention has been explained in relation to its preferred embodiment, it is to be understood that many other possible modifications and variations can be made without departing from the spirit and scope of the invention as hereinafter claimed.

What is claimed is:

1. A hygiene maintenance wristband comprises:
   a band;
   a first casing;
   a second casing;
   a solution dispenser;
   a clasp mechanism;
   the band comprises a fixed member and an adjustable member;
   a first end of the adjustable member and a first end of the fixed member being fixed with the first casing;
   the first end of the adjustable member being positioned opposite the first end of the fixed member about the first casing;
   a second end of the fixed member being connected with the second casing;
   a second end of the adjustable member being operatively coupled with the second casing by the clasp mechanism, wherein the clasp mechanism is used to readily connect or readily disconnect the adjustable member to the second casing and wherein the clasp mechanism is used to lengthen or shorten a combined circumference of the band;
   the second end of the adjustable member being positioned opposite the second end of the fixed member about the second casing;

the solution dispenser being integrated into the first casing, opposite the second casing;
a dispenser-release mechanism;
the first casing comprises a base wall and a lateral wall;
the solution dispenser comprises a frame, an annular retainer, and at least one pod;
the base wall being positioned adjacent with the lateral wall;
the lateral wall being perimetrically fixed around the base wall;
the frame being positioned within the lateral wall;
the annular retainer being mounted onto the frame;
the annular retainer being removably attached around the at least one pod; and
the frame being operatively coupled with the lateral wall by the dispenser-release mechanism, wherein the dispenser-release mechanism is used to lock or unlock the frame with the lateral wall.

2. The hygiene maintenance wristband as claimed in claim 1 comprises:
the clasp mechanism comprises a main release button, a safety release button, a ratchet mechanism, a first slot, and a second slot;
the band comprises a plurality of tracks;
the plurality of tracks being integrated along the adjustable member;
the main release button and the safety release button being positioned opposite each other about the second casing;
the main release button and the safety release button being externally integrated into the second casing;
the first slot laterally traversing into the second casing;
the second slot laterally traversing into the second casing, opposite the first slot;
the second end of the fixed member being connected within the second slot;
the second end of the adjustable member being operatively coupled within the first slot by an engagement between the ratchet mechanism and the plurality of tracks, wherein the ratchet mechanism is used to readily engage or readily disengage the plurality of tracks; and,
the main release button and the safety release button being operatively coupled with the ratchet mechanism, wherein the main release button and the safety button are simultaneously pressed in order to release the ratchet mechanism.

3. The hygiene maintenance wristband as claimed in claim 1 comprises:
the solution dispenser comprises a frame, an annular retainer, at least one pod, a pod-releasing mechanism, a retractable nozzle, and a release switch;
the annular retainer being attached around the at least one pod;
the annular retainer being operatively coupled to the frame by the pod-releasing mechanism, wherein the pod-releasing mechanism is used to extend the frame out of the second casing and is used to then rotate the annular retainer; and,
the release switch being operatively coupled to the pod-releasing mechanism, wherein the release switch is used to actuate the pod-releasing mechanism.

4. The hygiene maintenance wristband as claimed in claim 3 comprises:
the pod-releasing mechanism comprises a control button and a couple of rail assemblies;
each of the couple of rail assemblies comprises a stopper end and a rotation end;
the stopper end being positioned opposite the rotation end along the rail assembly;
the annular retainer being rotatably mounted with the rotation end;
the control button being externally mounted with the frame;
the at least one pod being slidably engaged along the couple of rail assemblies; and,
the control button being operatively coupled to the rotation end of each of the couple of rail assemblies, wherein the control button is used to actuate the rotation end and is consequently used to flip the at least one pod.

5. The hygiene maintenance wristband as claimed in claim 3 comprises:
the retractable nozzle being telescopic.

6. The hygiene maintenance wristband as claimed in claim 3 comprises:
the solution dispenser further comprises a bacteria-detecting light source; and,
the bacteria-detecting light source being externally integrated with the frame.

7. The hygiene maintenance wristband as claimed in claim 1 comprises:
the solution dispenser comprises at least one pod;
the at least one pod comprises a first retaining portion, a second retaining portion, and a disk plate;
the first retaining portion being mounted onto the disk plate; and,
the second retaining portion being mounted onto the disk plate, opposite the first retaining portion.

8. The hygiene maintenance wristband as claimed in claim 1 comprises:
a portable computing device;
the portable computing device comprises a main display screen, at least one light source, a speaker, a microphone, a camera, at least one biometric sensor, a microprocessor, and a power source;
the main display screen, the speaker, the microphone, and the camera being externally integrated into a first flat surface of the second casing;
a second flat surface being positioned opposite the first flat surface about the second casing;
the at least one biometric sensor being externally integrated into the second flat surface;
the at least one light source being laterally mounted with the second casing in between the first flat surface and the second flat surface;
the microprocessor and the power source being mounted within the second casing;
the microprocessor being electronically connected with the main display screen, the at least one light source, the speaker, the microphone, the camera, the at least one biometric sensor, and the power source; and,
the power source being electrically connected with the main display screen, at least one light source, the speaker, the microphone, the camera, the at least one biometric sensor, and the microprocessor.

9. The hygiene maintenance wristband as claimed in claim 1 comprises:
a floss-dispensing mechanism; and,
the floss-dispensing mechanism being laterally integrated into the second casing.

10. A hygiene maintenance wristband comprises:
a band;
a first casing;
a second casing;

a solution dispenser;
a clasp mechanism;
a portable computing device;
the band comprises a fixed member and an adjustable member;
a first end of the adjustable member and a first end of the fixed member being fixed with the first casing;
the first end of the adjustable member being positioned opposite the first end of the fixed member about the first casing;
a second end of the fixed member being connected with the second casing;
a second end of the adjustable member being operatively coupled with the second casing by the clasp mechanism, wherein the clasp mechanism is used to readily connect or readily disconnect the adjustable member to the second casing and wherein the clasp mechanism is used to lengthen or shorten a combined circumference of the band;
the second end of the adjustable member being positioned opposite the second end of the fixed member about the second casing;
the solution dispenser being integrated into the first casing, opposite the second casing;
the portable computing device comprises a main display screen, at least one light source, a speaker, a microphone, a camera, at least one biometric sensor, a microprocessor, and a power source;
the main display screen, the speaker, the microphone, and the camera being externally integrated into a first flat surface of the second casing;
a second flat surface being positioned opposite the first flat surface about the second casing;
the at least one biometric sensor being externally integrated into the second flat surface;
the at least one light source being laterally mounted with the second casing in between the first flat surface and the second flat surface;
the microprocessor and the power source being mounted within the second casing;
the microprocessor being electronically connected with the main display screen, the at least one light source, the speaker, the microphone, the camera, the at least one biometric sensor, and the power source; and,
the power source being electrically connected with the main display screen, at least one light source, the speaker, the microphone, the camera, the at least one biometric sensor, and the microprocessor.

11. The hygiene maintenance wristband as claimed in claim 10 comprises:
the clasp mechanism comprises a main release button, a safety release button, a ratchet mechanism, a first slot, and a second slot;
the band comprises a plurality of tracks;
the plurality of tracks being integrated along the adjustable member;
the main release button and the safety release button being positioned opposite each other about the second casing;
the main release button and the safety release button being externally integrated into the second casing;
the first slot laterally traversing into the second casing;
the second slot laterally traversing into the second casing, opposite the first slot;
the second end of the fixed member being connected within the second slot;
the second end of the adjustable member being operatively coupled within the first slot by an engagement between the ratchet mechanism and the plurality of tracks, wherein the ratchet mechanism is used to readily engage or readily disengage the plurality of tracks; and,
the main release button and the safety release button being operatively coupled with the ratchet mechanism, wherein the main release button and the safety button are simultaneously pressed in order to release the ratchet mechanism.

12. The hygiene maintenance wristband as claimed in claim 10 comprises:
a dispenser-release mechanism;
the first casing comprises a base wall and a lateral wall;
the solution dispenser comprises a frame, an annular retainer, and at least one pod;
the base wall being positioned adjacent with the lateral wall;
the lateral wall being perimetrically fixed around the base wall;
the frame being positioned within the lateral wall;
the annular retainer being mounted onto the frame;
the annular retainer being removably attached around the at least one pod; and,
the frame being operatively coupled with the lateral wall by the dispenser-release mechanism, wherein the dispenser-release mechanism is used to lock or unlock the frame with the lateral wall.

13. The hygiene maintenance wristband as claimed in claim 10 comprises:
the solution dispenser comprises a frame, an annular retainer, at least one pod, a pod-releasing mechanism, a retractable nozzle, and a release switch;
the annular retainer being attached around the at least one pod;
the annular retainer being operatively coupled to the frame by the pod-releasing mechanism, wherein the pod-releasing mechanism is used to extend the frame out of the second casing and is used to then rotate the annular retainer;
the retractable nozzle being telescopic and,
the release switch being operatively coupled to the pod-releasing mechanism, wherein the release switch is used to actuate the pod-releasing mechanism.

14. The hygiene maintenance wristband as claimed in claim 13 comprises:
the pod-releasing mechanism comprises a control button and a couple of rail assemblies;
each of the couple of rail assemblies comprises a stopper end and a rotation end;
the stopper end being positioned opposite the rotation end along the rail assembly;
the annular retainer being rotatably mounted with the rotation end;
the control button being externally mounted with the frame;
the at least one pod being slidably engaged along the couple of rail assemblies; and,
the control button being operatively coupled to the rotation end of each of the couple of rail assemblies, wherein the control button is used to actuate the rotation end and is consequently used to flip the at least one pod.

15. The hygiene maintenance wristband as claimed in claim 13 comprises:
the solution dispenser further comprises a bacteria-detecting light source; and, the bacteria-detecting light source being externally integrated with the frame.

16. The hygiene maintenance wristband as claimed in claim 10 comprises:
   the solution dispenser comprises at least one pod;
   the at least one pod comprises a first retaining portion, a second retaining portion, and a disk plate;
   the first retaining portion being mounted onto the disk plate; and,
   the second retaining portion being mounted onto the disk plate, opposite the first retaining portion.

17. The hygiene maintenance wristband as claimed in claim 10 comprises:
   a floss-dispensing mechanism; and,
   the floss-dispensing mechanism being laterally integrated into the second casing.

\* \* \* \* \*